United States Patent [19]

Sheldon

[11] Patent Number: 5,725,562

[45] Date of Patent: Mar. 10, 1998

[54] RATE RESPONSIVE CARDIAC PACEMAKER AND METHOD FOR DISCRIMINATING STAIR CLIMBING FROM OTHER ACTIVITIES

[76] Inventor: Todd J. Sheldon, 3889 Princeton Trail, Eagan, Minn. 55123

[21] Appl. No.: 668,524

[22] Filed: Jun. 28, 1996

Related U.S. Application Data

[63] Continuation-in-part of Ser. No. 413,733, Mar. 30, 1995, abandoned.

[51] Int. Cl.⁶ ................................................ A61N 1/365
[52] U.S. Cl. .................................................... 607/19
[58] Field of Search ............................. 607/17, 19, 62

[56] References Cited

U.S. PATENT DOCUMENTS

| | | |
|---|---|---|
| 4,257,423 | 3/1981 | McDonald . |
| 4,374,382 | 2/1983 | Markowitz . |
| 4,428,378 | 1/1984 | Anderson . |
| 4,556,063 | 12/1985 | Thompson . |
| 4,771,780 | 9/1988 | Sholder ................................ 607/19 |
| 4,869,251 | 9/1989 | Lekholm . |
| 5,010,893 | 4/1991 | Sholder . |
| 5,031,618 | 7/1991 | Mullett . |
| 5,127,404 | 7/1992 | Wyborny . |
| 5,226,413 | 7/1993 | Bennett . |
| 5,233,984 | 8/1993 | Thompson . |
| 5,354,317 | 10/1994 | Alt . |
| 5,383,911 | 1/1995 | Mann ................................. 607/17 |
| 5,472,453 | 12/1995 | Alt ................................... 607/19 |

OTHER PUBLICATIONS

Bacharach et al., "Activity–Based Pacing: Comparison of a Device Using an Accelerometer Versus a Piezoelectric Crystal" *PACE*, vol. 15, pp. 188–196, Feb. 1992.

Alt et al., "A New Mechanical Sensor for Detecting Body Activity and Posture, Suitable for Rate Responsive Pacing", *PACE*, vol. 11, pp. 1875–81, Nov. 1988, Part II.

"Airbags Boom When IC Accelerometer Sees 50G", *Electronic Design*, Aug. 8, 1991.

"Monolithic Accelerometer with Signal Conditioning", Rev. O, published Jun. 1993 by Analog Devices, Inc.

*Primary Examiner*—William E. Kamm
*Attorney, Agent, or Firm*—Michael B. Atlass; Harold R. Patton

[57] ABSTRACT

A method of and apparatus for pacing a patient's heart at a pacing rate dependent on patient activity and posture particularly during stair climbing. A dual chamber, rate responsive pacemaker for pacing a patient's heart includes at least one DC accelerometer mounted in the pacemaker pulse generator for implantation such that the sensitive axis of the DC accelerometer is sensitive to the effects of gravity during forward lean of the patient characteristic of stair climbing posture. The DC and AC signal outputs of the accelerometer are processed to develop a tilt signal and an activity signal. A target rate control signal is derived from the activity signal dependent on the level of activity. A stair climbing rate is selected for controlling the physiologic pacing rate between a lower and an upper pacing rate in the presence of an activity signal indicative of a patient walking rate and a tilt signal value falling within a tilt window. The target rate control signal is used to control the pacing rate if the activity signal is indicative of faster patient movement, e.g. running, or if the tilt signal is outside the tilt window indicating that the patient is either upright or prone.

27 Claims, 8 Drawing Sheets

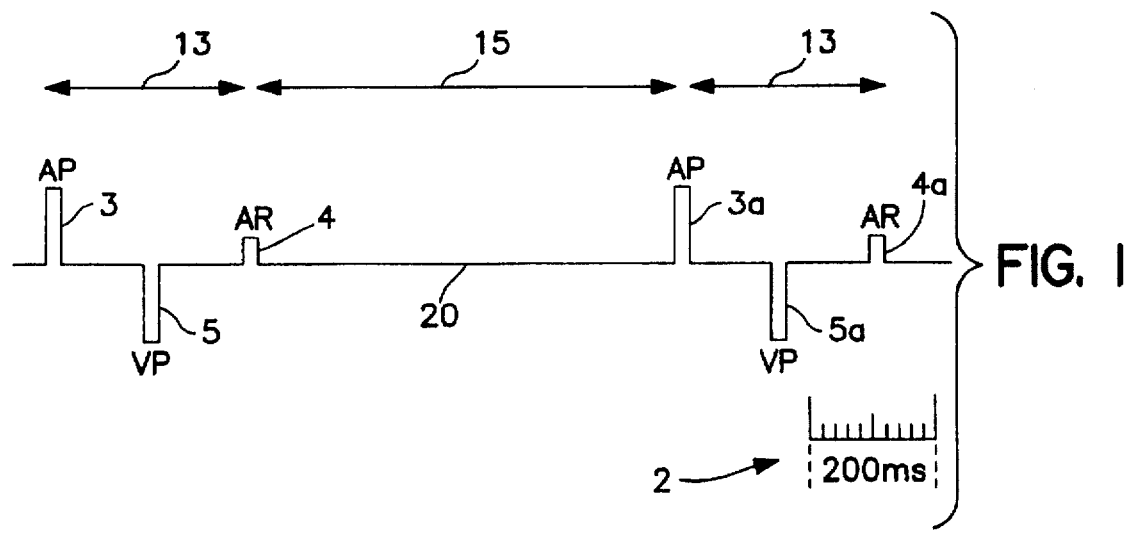
FIG. 1
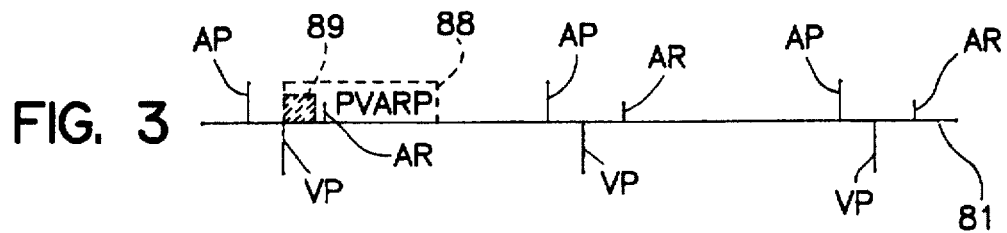
FIG. 3
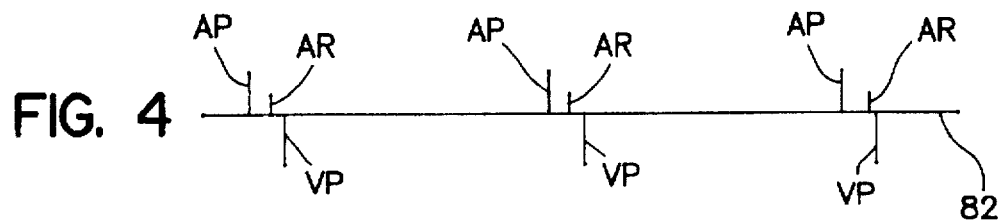
FIG. 4
FIG. 5
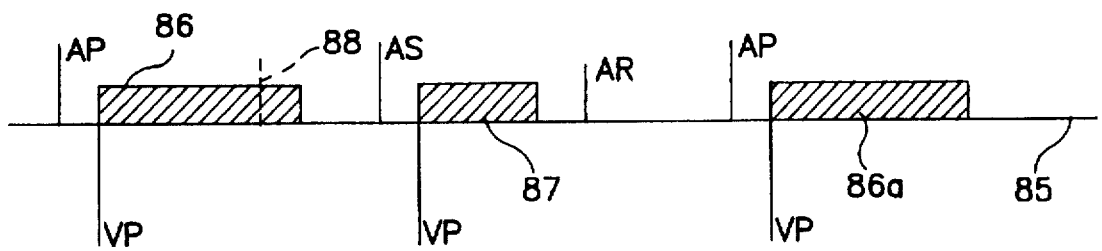

METHOD 3: IF SEQUENCE IS AR-AP AND MAI WAS DECREMENTED
ON LAST UPDATE, THEN ADD CORRECTION FACTOR TO MAI

RATE RESPONSIVE CARDIAC PACEMAKER AND METHOD FOR DISCRIMINATING STAIR CLIMBING FROM OTHER ACTIVITIES

This application is a continuation-in-part of application Ser. No. 08/413,733, filed Mar. 30, 1995, now abandoned.

REFERENCE TO RELATED APPLICATION

Reference is made to commonly assigned co-pending U.S. patent application Ser. No. 413,736 filed even date herewith entitled MEDICAL DEVICE EMPLOYING MULTIPLE DC ACCELEROMETERS FOR PATIENT ACTIVITY AND POSTURE SENSING filed on even date herewith

BACKGROUND OF THE INVENTION

1. Field of the Invention

The present invention relates to rate responsive cardiac pacemakers and more particularly to the use of a DC accelerometer for detection of patient posture and activity level, particularly to provide appropriate pacing rates during stair climbing and descending.

2. Description of the Prior Art

Rate responsive pacing has been widely adopted for adjusting pacing rate to the physiologic needs of the patient in relatively recent years. Early single chamber cardiac pacemakers provided a fixed rate stimulation pulse generator that could be reset, on demand, by sensed atrial or ventricular contractions recurring at a rate above the fixed rate. Later, dual chamber demand pacemakers became available for implantation in patients having an intact atrial sinus rate but no AV conduction, so that ventricular pacing could be synchronized with the atrial sinus rate, and backup fixed rate ventricular pacing could be provided on failure to sense atrial depolarizations. In addition, rate programmable pacemakers became available wherein the base pacing rate could be selected by a physician to provide a compromise fixed rate that did not interfere with patient rest and provided adequate cardiac output at moderate levels of exercise.

Such fixed rate pacing, particularly for patients not having an adequate atrial sinus rate to allow synchronous pacing, left most patients without the ability to exercise, lift objects or even walk up stairs without suffering loss of breath due to insufficient cardiac output. However, the introduction of the Medtronic® Activitrax® pacemaker provided patients with the a pulse generator having a rate responsive capability dependent on the level of patient activity. A piezoelectric crystal bonded to the interior of the implantable pulse generator can or case is employed in that pacemaker and successor models to provide a pulse output signal related to the pressure wave generated by a patient's footfall and conducted through the body to the crystal. Thus, low frequency activity signals recurring at the patient's rate of walking or running could be sensed and processed to derive a pacing rate appropriate to the level of activity. The activity sensor and its operation is described in commonly assigned U.S. Pat. No. 4,428,378 to Anderson.

Since the introduction of the Activitrax® pacemaker, a great many rate responsive pacemakers employing a wide variety of activity sensors and other physiologic sensors have been proposed and marketed. A comprehensive listing of such rate responsive pacemakers, sensors and sensed physiologic parameters is set forth in commonly assigned U.S. Pat. No. 5,226,413 to Bennett et al., incorporated herein by reference. However, the activity sensor of the type employed in the Activitrax® pacemaker continues to be used in successor single and dual chamber, rate responsive pacemaker models and remains the most widely used physiologic sensor.

As mentioned above, this piezoelectric crystal sensor is responsive to pressure waves generated by patient footfalls striking the exterior of the pulse generator case. Activity sensor configurations employing integrated circuit, AC accelerometers on an IC chip inside the pacemaker are also being employed in the EXCEL"VR pacemaker sold by Cardiac Pacemakers, Inc., and in similar rate responsive pacemakers sold by other manufacturers. The AC accelerometer is formed of a silicon beam mass suspended on the IC that swings or moves in response to shock waves caused by body motion and provides an output signal having a magnitude dependent on the rate of movement.

The relative virtues and weaknesses of piezoelectric crystal and AC accelerometer activity sensors and associated pacemakers are reported widely, e.g. in the article "Activity-Based Pacing: Comparison of a Device Using an Accelerometer Versus a Piezoelectric Crystal", by Bacharach et al. (*PACE*, Vol 15, pp. 188–196, February 1992). As indicated in that article, the pacing rate responses of these pacemakers strapped on patients with normal hearts who were subjected to various stress tests were measured and compared to each other and to the patients' average actual heart rates. The tests conducted included stair ascending or climbing and descending tests, and conclusions were drawn to the effect that the AC accelerometer performed superiorly to the piezoelectric sensor in certain respects. Higher cardiac output is required in ascending a flight of stairs than in walking at the same rate or in descending the flight of stairs at the same rate as indicated by the patients' heart rates. The reported AC accelerometer induced pacing rate during stair climbing more closely matched the required cardiac output as indicated by the test subjects' average heart rates. During stair descending, the AC accelerometer induced pacing rate did not appreciably fall and exceeded the patients' actual heart rate. The reported piezoelectric sensor induced pacing rate during stair climbing fell below the required cardiac output as indicated by the test subjects' average heart rates. During stair descending, the piezoelectric crystal induced pacing rate increased from the rate achieved during ascending and also exceeded the patients' heart rate.

As a result, while the authors suggest that the AC accelerometer is superior in certain respects to the piezoelectric crystal sensor, the test data also indicates that the AC accelerometers do not adequately distinguish between stair ascending and descending or walking at the same rate on a flat surface to set an appropriate pacing rate. Neither the AC accelerometer nor the piezoelectric sensor can inherently distinguish these patient activities. If an appropriate rate for an individual patient is set for stair climbing, for example, that rate may only be triggered by the frequency of recurrence of the patient footfalls and consequently may be too high a rate for either stair descending or level walking at the same speed.

Like the piezoelectric crystal sensor, there is no signal output from the AC accelerometer in the absence of body motion and related to body position or attitude. In other words, when a patient is at rest, neither activity sensor provides any indication as to whether the patient is upright and awake and resting or lying down and presumably sleeping or resting. Other sensors for sensing physiologic parameters induced by high levels of exercise have been proposed to detect the physiologic changes accompanying exercise, rest and sleep to trigger appropriate rates. To lower the pacing rate during sleep, the inclusion of a real time clock to establish a Circadian rhythm pacing rate has also been proposed. None of these proposed sensors or systems are capable of determining a patient's position or posture.

A mechanical sensor has been proposed in the article "A New Mechanical Sensor for Detecting Body Activity and Posture, Suitable for Rate Responsive Pacing" by Alt et al. (*PACE*, Vol.11, pp. 1875–81, November, 1988, Part II) and in U.S. Pat. No. 4,846,195 that involves use of a multi-contact, tilt switch. This switch employs a mercury ball within a container that is proposed to be fixed in the pulse generator case, so that if the pulse generator is implanted at a certain orientation, and stays in that orientation, certain contacts are closed by the mercury ball when the patient is upright and others are closed or none are closed when the patient is prostrate, i.e., either prone or supine. During movement of the body, the mercury ball is expected to jiggle randomly and the number of contacts made per unit of time may be used as a measure of the level of activity. Similar sensors have been proposed in U.S. Pat. Nos. 4,869,251, 5,010,893, 5,031,618 and 5,233,984.

The use of elemental mercury is generally not favored and would increase environmental problems related to disposal of the pulse generators after use. Long term contact contamination and bridging issues would also arise, particularly given the extremely small size of the switch for confinement within modern pulse generator cases.

Presumably, the multi-contact tilt switch sensor would also not necessarily be able to distinguish between stair climbing and descending at the same stepping rate. Given the necessary small size of the tilt switch, it would be difficult to accurately position the pacemaker pulse generator so that consistent, reproducible signal outputs from the sets of contacts bridged while stooped forward or rearward would be achieved in a given patient over time. Moreover, the limited number of contacts reduce the possibility that such discrimination could be achieved. To date, no implants of pacemaker pulse generators using such a tilt switch have been reported.

More recently, the use of a solid state position sensor in the form of a DC accelerometer is proposed in U.S. Pat. No. 5,354,317. The DC accelerometer disclosed in the '317 patent is fabricated in hybrid semiconductor IC form as a polycrystalline silicon, square plate, suspended at its four corners above a well in a single silicon crystal substrate, and associated low pass filter circuits are formed on the same substrate. The suspended plate structure moves between stationary positions with respect to the well on the suspension arms in response to earth gravity, depending on its orientation to the gravitational field. The plate also vibrates on the suspension arms similar to the AC accelerometer in response to acceleration movements of the patient's body.

The single DC accelerometer of the '317 patent is oriented to be sensitive to the anterior-posterior axis of the patient so that the upright, supine and prone body positions can be discriminated, and separate base pacing rates can be set. Rate changes from the base pacing rates dependent on the exercise level of the patient in each position are suggested. When changes in patient position are detected in the absence of physical exercise, the base pacing rate change is smoothed between the old and new rate to avoid a sudden step change.

The signal processing of the output signal from the single DC accelerometer of the '317 patent includes signal level calibration for each individual patient to account for differences in the angle of orientation of the DC accelerometer plate resulting from the implantation angle of the pulse generator case in the patient's body. However, this calibration is not suggested in order to distinguish body positions having a more or less common angular relation of the movable plate to the gravitational field.

In addition, the '317 patent does not appear to suggest any discrimination of stair climbing that would alleviate the problems identified above resulting in the same or a higher pacing rate being developed during stair descending than during stair climbing.

Despite the weaknesses reported with respect to the piezoelectric sensors and solid state accelerometers, they remain favored over the other physiologic sensors that have been proposed or are in clinical use due to their relative simplicity, reliability, predictability, size, and low cost.

Problems to be Solved by the Invention

In view of the demonstrated advantages of the piezoelectric and AC accelerometer type activity sensors, it would be desirable to employ solid state sensors responsive to patient activity in a similar manner that would also distinguish stair or steep incline climbing from other activities in order to provide an appropriate rate response to provide adequate cardiac output.

SUMMARY OF THE INVENTION

In view of the above, it is an object of the present invention to provide a rate responsive pacemaker employing a body position sensor to distinguish stair climbing from other activities, e.g. stair descending or walking on a level surface, and to provide an appropriate pacing rate increase from a rest rate during stair climbing.

It is yet a further particular object of the present invention to provide such pacing rate setting capabilities to provide a higher pacing rate for a patient ascending stairs or a steep incline than descending stairs or walking on a relatively level surface.

There is provided in accordance with the present invention, a rate responsive pacemaker for pacing a patient's heart at a pacing rate dependent on patient activity and posture particularly during stair climbing, at least including the means for and steps of:

deriving a body posture tilt signal having a characteristic varying with the degree to which the patient posture is in an upright stance or leaning forward;

detecting patient footsteps;

deriving a patient activity signal having a signal level dependent on the frequency of patient footsteps recurring over a time unit;

deriving a rate control signal from the body posture tilt signal and the patient activity signal correlated to the physiologic demand on the patient's heart;

defining physiologic escape intervals as a function of the rate control signal to establish a physiologic pacing rate;

generating pacing pulses at the physiologic pacing rate; and applying the pacing pulses to the patient's heart.

Preferably, the posture of the patient is determined through the use of a solid state, DC accelerometer mounted within the pacemaker pulse generator case having a sensitive axis aligned with the pacemaker case and the patient's anterior-posterior (A-P) body axis. The DC accelerometer provides an output signal due to the force of gravity which has a polarity and magnitude dependent on the degree to which the sensitive axis is tilted forward or rearward from the direction of earth's gravity. Forward lean or tilt of the patient while upright accompanied by a recurring series of footfalls can be distinguished from an upright stance and a similar level of footfalls to thereby distinguish stair climbing from other activities in the same stepping rate range and provide an appropriate pacing rate for each activity.

The DC accelerometer is preferably mounted into an IC chip with a second and optionally a third DC accelerometer so that their sensitive axes are aligned with the three axes of the pulse generator case. The physician can implant and stabilize the pulse generator case in the proper orientation to the patient's thorax to align the sensitive axes with the superior-inferior (S-I), anterior-posterior (A-P), and lateral-medial (L-M) axes of the chest cavity. As a result, distinctive signal levels are developed by each DC accelerometer in each posture position due to the effect of gravity on the sensitive axis of each semiconductor element. From these signal levels, the posture of the patient can be determined for providing additional pacing rates appropriate to the other determined body positions and the activity level of the patient.

Advantageously, one or more of the DC accelerometers can be used to derive the level of patient activity from the number of changes in signal levels exceeding a certain threshold occurring in a given sampling time period, as is conventional in use of the piezoelectric and AC accelerometer activity sensors described above.

The present invention may also be implemented employing other forms of body position or tilt sensors having a sensitive axis in the A-P direction, particularly the sensor disclosed in the above-referenced '984 patent.

It should be noted that the DC accelerometer of the above-referenced '317 patent is a bulk micromachined IC structure that has a sensitive axis normal to the plane of the movable plate and provides the +1, −1 and 0 static output signal levels depending on the orientation of the sensitive axis to the vertical gravitational force. If such a DC accelerometer is used in the practice of the present invention, the orthogonally arranged DC accelerometers would provide similar signal responses as long as the sensitive axes are oriented in the same manner as described above.

Advantages of the Invention

The DC output signal of a DC accelerometer can be processed to detect body forward tilt, while the patient moves at a walking pace, and thereby employed to discriminate stair climbing from other activities and to develop an appropriate pacing rate, solving the problems associated with the prior art rate responsive pacemakers employing activity sensors. The DC accelerometer and associated circuitry can be easily incorporated into a pacemaker pulse generator at low cost. The ease of use, and the reproducibility and consistency of results attained will lead to acceptability within the medical community.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIG. 1 is block level diagram of a DDDR pacemaker capable of implementing at least one of three possible, mutually orthogonal DC accelerometers as activity and patient posture sensors particularly to detect forward tilt;

FIG. 3 is a rate response overview flowchart of the algorithm incorporated into the pacemaker of FIG. 1 for deriving a physiologic pacing rate related to stair climbing from the output signal of the DC accelerometer of FIG. 2 oriented along its sensitive axis in the A-P direction;

FIG. 4 is a detailed flowchart of the stair climbing discrimination step of the flowchart of FIG. 3;

FIG. 5 is a detailed flowchart of the discrimination rate calculation step of the flowchart of FIG. 3;

DETAILED DESCRIPTION OF THE PREFERRED EMBODIMENTS

Figure 2:
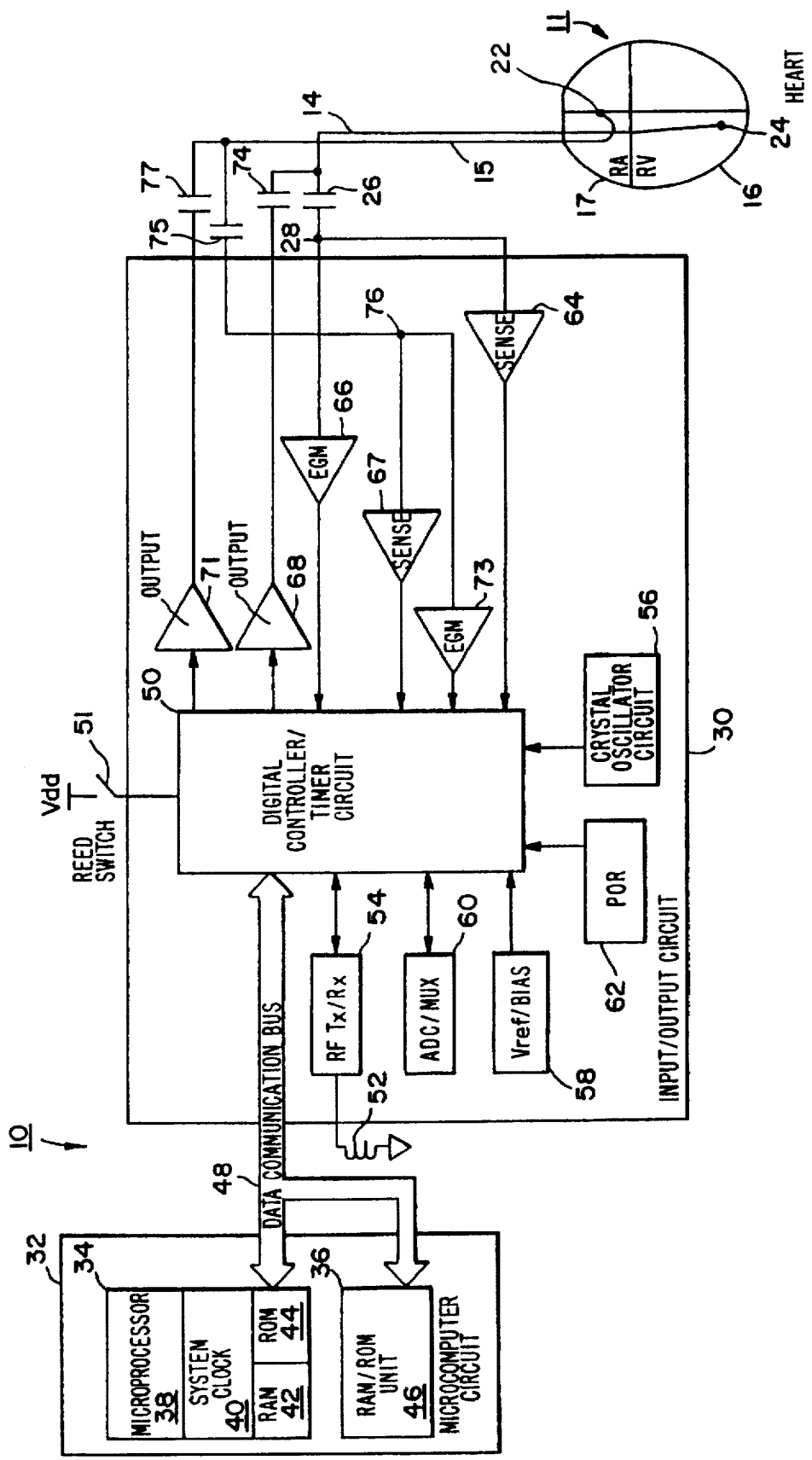
FIG. 2 is a schematic illustration of the orientations of the S-I, L-M, and A-P sensitive axes of three DC accelerometers mounted orthogonally with respect to a hybrid circuit substrate mounted within the housing for the pulse generator of FIG. 1 and the markings on the housing for orienting the pulse generator with the patient body axes.
Figure 7C:
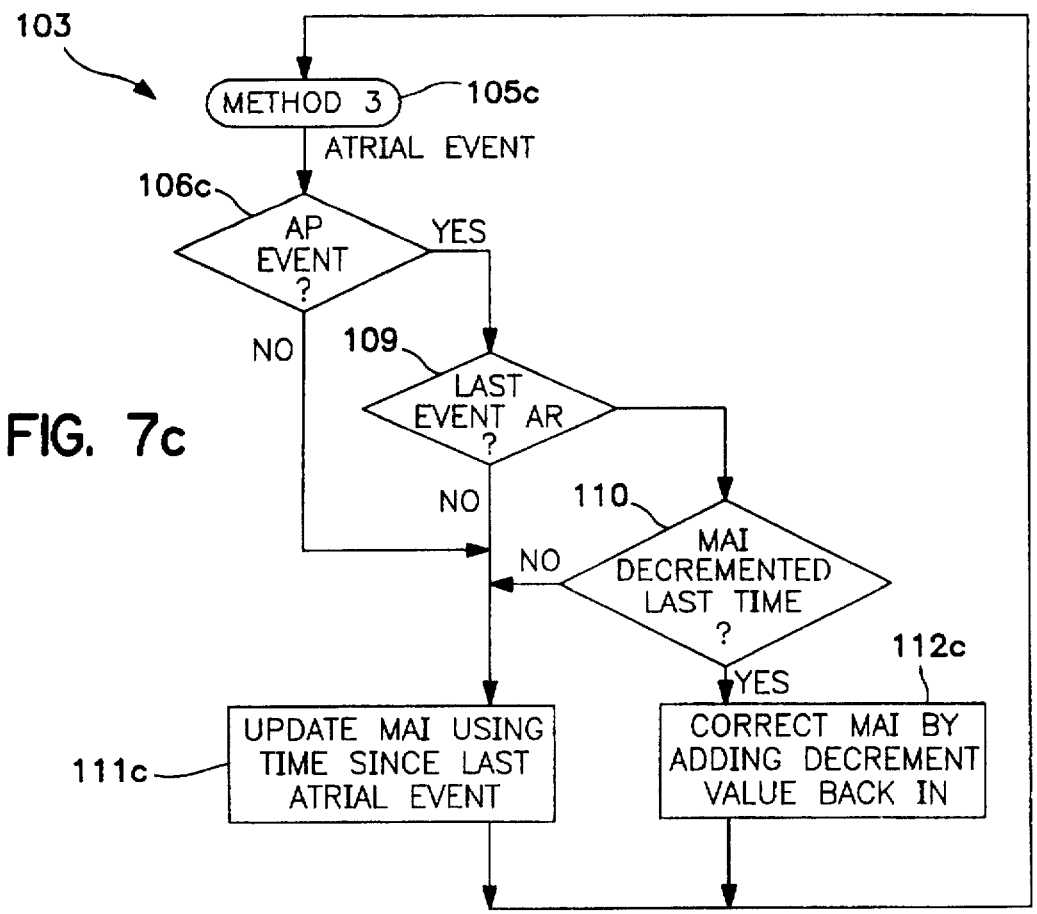
FIGS. 7–9 are graphs illustrating the tilt deviation distributions resulting from of tests conducted on test subjects employing the stair climbing discrimination algorithm of FIGS. 3–5.

The present invention is preferably implemented in multi-programmable DDDR pacemakers of types widely known in the prior art. However, the invention could be implemented in simpler, single chamber pacemakers. As described above with respect to other medical devices, the invention may also be implemented in other medical devices for providing other therapies and/or for monitoring physiologic parameters in the various body positions the patient may assume where stair climbing discrimination may be important.

FIG. 1 is block level diagram of such a pacemaker implantable pulse generator or IPG 30 and lead set 12 and 14 which sets forth the structures required to incorporate the invention into a DDDR pacemaker. In the drawing, the patient's heart 10 has an atrial pacing lead 12 passed into the right atrium and a ventricular lead 14 passed into the right ventricle. The atrial lead 12 has an atrial electrode array 16 which couples the pulse generator 30 to the atrium. The ventricular lead 14 has a ventricular electrode array 18 for coupling the pulse generator 30 to the ventricle of the patient's heart 10. Atrial and ventricular leads 12 and 14 are depicted as bipolar leads coupled to a bipolar IPG 30, although unipolar leads could be employed with a suitable IPG.

The IPG circuit 30 of FIG. 1 is divided generally into a pacing circuit 32 coupled to a battery power supply 50, an activity sensor 60 of the type described below, a telemetry coil 45 and a microcomputer circuit 34. The pacing circuit 32 includes the atrial and ventricular output amplifier circuit 36 and sense amplifiers 38 that are coupled to the atrial and ventricular leads 12 and 14, respectively, the digital controller/timer circuit 40 and other associated components described below. The output circuit 36 and sense amplifier circuit 38 may contain atrial and ventricular pulse generators and sense amplifiers corresponding to any of those presently employed in commercially marketed dual chamber cardiac pacemakers.

Sensed atrial depolarizations (A-SENSE) or P-waves that are confirmed by the atrial sense amplifier are communicated to the digital controller/timer circuit 40 on the ASE line. Similarly, ventricular depolarizations (V-SENSE) or R-waves that are confirmed by the ventricular sense amplifier are communicated to the digital controller/timer circuit 40 on VSE. The sensitivity control block 42 adjusts sensitivity of each sense amplifier in response to control signals provided by digital controller/timer 40 that are in turn stored in memory in microcomputer circuit 34 and from which the various tilt signals hereinafter described are derived.

In order to trigger generation of a ventricular pacing or VPE pulse, digital controller/timer circuit 40 generates a trigger signal on the V-trig line. Similarly, in order to trigger an atrial pacing or APE pulse, digital controller/timer circuit 40 generates a trigger pulse on A-trig line.

Crystal oscillator circuit 44 provides the basic timing clock for the pacing circuit 30, while battery 50 provides power. Reference mode circuit 48 generates stable voltage reference and current levels for the analog circuits within the pacing circuit 30 from the battery voltage and current. Power-on-reset circuit 46 responds to initial connection of the circuit 30 to the battery 50 for defining an initial operating condition and also resets the operating condition in response to detection of a low battery energy condition. Analog to digital converter (ADC) and multiplexor circuit 52 digitizes analog signals and voltage to provide real time telemetry of ASE and VSE cardiac signals from sense amplifiers 38, for uplink transmission via RF transmitter and receiver circuit 47. Voltage reference and bias circuit 48, ADC and multiplexor 52, power-on-reset circuit 46 and crystal oscillator circuit 44 may correspond to any of those presently used in current marketed implantable cardiac pacemakers.

Data transmission to and from an external programmer (not shown) is accomplished by means of the telemetry antenna 45 and the associated RF transmitter and receiver 47, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. and U.S. Pat. No. 4,374,382 issued to Markowitz. Uplink telemetry capabilities will typically include the ability to transmit stored digital information as well as real time or stored EGMs of atrial and/or ventricular electrical activity (according to the teaching of the above-cited Wyborny patent), as well as transmission of Marker Channel pulses indicating the occurrence of sensed and paced depolarizations in the atrium and ventricle, as disclosed in the cited Markowitz patent.

Control of timing and other functions within the pacing circuit 30 is provided by digital controller/timer circuit 40 which includes a set of timers and associated logic circuits connected with the microcomputer 34. Microcomputer 34 controls the operational functions of digital controller/timer 40, specifying which timing intervals are employed, and controlling the duration of the various timing intervals, via data and control bus 56. Microcomputer 34 contains a microprocessor 54, associated system clock 58, and on-processor RAM and ROM chips 64 and 66, respectively. In addition, microcomputer circuit 34 includes a separate RAM/ROM chip 68 to provide additional memory capacity. Microprocessor 54 is interrupt driven, operating in a reduced power consumption mode normally, and awakened in response to defined interrupt events, which may include the A-trig, V-trig, ASE and VSE signals. The specific values of the intervals defined are controlled by the microcomputer circuit 54 by means of data and control bus 56 from programmed-in parameter values and operating modes.

If the IPG is programmed to a rate responsive mode, the patient's activity level is monitored periodically, and the a sensor derived pacing escape interval is adjusted proportionally. A timed interrupt, e.g., every two seconds, may be provided in order to allow the microprocessor 54 to analyze the output of the activity circuit (PAS) 62 and update the basic V-A escape interval employed in the pacing cycle. In the DDDR mode, the V-A escape interval may be selected as the variable pacing rate establishing interval, but the A-V interval and the atrial and ventricular refractory periods may also vary with the V-A escape interval established in response to patient activity.

Preferably, two separate lower rate V-A interval timer functions are provided. The first is set by the physician when the base pacing rate is selected. This DDD V-A time interval starts from the occurrence of a VPE or VPE, and provided neither an ASE nor a VSE occurs during the V-A time interval, an APE is generated after the expiration of the V-A time interval. The duration of the second lower rate time interval is a function of the measured patient activity acquired by the activity sensor 21. Typically, this DDDR, V-A time interval begins with a VSE or VPE and has a time duration reflecting patient activity. In this art, such structures are well known, and a variety of techniques can be used to implement the required timer functions.

Digital controller/timer circuit 40 starts and times out these and other intervals employed over a pacing cycle comprising a successive A-V and V-A interval in a manner well known in the art. Typically, digital controller/timer circuit 40 defines an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 40 also defines the atrial refractory period (ARP) during which atrial sensing is disabled or the ASE is ignored for the purpose of resetting the V-A escape interval. The ARP extends from the beginning of the A-V interval following either an ASE or an A-trig and until a predetermined time following sensing of a ventricular depolarization or triggering the delivery of a VPE pulse. A post-ventricular atrial refractory period (PVARP) is also defined following delivery of a VPE pulse. The durations of the ARP, PVARP and VRP may also be selected as a programmable parameter stored in the microcomputer 34. Digital controller/timer circuit 40 also controls the pulse widths of the APE and VPE pacing pulses and the sensitivity settings of the sense amplifiers 38 by means of sensitivity control 42. Digital controller timer/logic circuit 40 also times out an upper rate limit interval (URL) set by a value programmed into memory in microcomputer circuit 34. This timer is initiated by the occurrence of a VPE or VSE, and limits the upper rate at which ventricular stimuli are delivered to the heart. The lower pacing rate is established by a programmed-in V-A or A-A interval value stored in memory in microcomputer circuit 34.

The illustrated IPG block diagram of FIG. 1 is merely exemplary, and corresponds to the general functional organization of most multi-programmable microprocessor controlled DDDR cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 66 of the microcomputer circuit 34. However, the present invention may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present invention should not be understood to be limited to a pacemaker having an architecture as illustrated in FIG. 1.

FIG. 2 is a schematic illustration of embodiment of a DC accelerometer based forward lean sensor that may be employed in the practice of the present invention. In FIG. 2, three solid state, DC accelerometers, namely the S-I DC accelerometer 72, A-P DC accelerometer 74, and L-M DC accelerometer 76, are mounted so that their sensitive axes are orthogonally directed to the S-I, A-P and L-M axes, respectively, of the pulse generator hybrid circuit substrate 76 and exterior case 78. In the practice of the present invention, the DC output signal of the A-P DC accelerometer 74 is preferably employed in the discrimination of stair climbing from other activities.

Each of the DC accelerometers 72, 74, 76 is preferably a surface micromachined integrated circuit with signal conditioning, e.g. the Model ADXL 50 accelerometer sold by Analog Devices, Inc., Norwood Mass. and described in detail in the article "Airbags Boom When IC Accelerometer Sees 50 G", in the Aug. 8, 1991, issue of *Electronic Design*, and in "Monolithic Accelerometer with Signal Conditioning", Rev. O, published by Analog Devices, Inc., both incorporated herein by reference in their entirety. Employing surface micromachining, a set of movable capacitor plates are formed extending in a pattern from a shaped polysilicon proof mass suspended by tethers with respect to a further set of fixed polysilicon capacitor plates. The proof mass has a sensitive axis along which a force between 0 G and +/–50 G effects physical movement of the proof mass and a change in measured capacitance between the fixed and movable plates. The measured capacitance is transformed by the on-chip signal conditioning circuits into a low voltage signal.

The proof mass of the ADXL 50 is co-planar with the IC chip plane it is tethered to for movement back and forth in positive and negative vector directions along a single sensitive axis. The planar orientation thus provides that the proof mass sensitive axis is along the length of the proof mass. For off the shelf use, the ADXL 50 IC chip is mounted in a TO-5 can with the positive vector direction of the sensitive axis aligned to a reference tab of the can. By using to the can tab, the positive or negative vector direction of the sensitive axis can be aligned with respect to some plane or angle of the system or circuit it is used in with respect to the constant vertical direction of gravitational force.

The reference tabs for the three axes are schematically illustrated in activity sensor 60 of FIG. 1 and with respect to each of the DC accelerometers 72, 74 and 76 of FIG. 2. Of course, in actual custom fabrication within the pulse generator 30, the DC accelerometers would be formed or assembled on a single IC chip and the assembly could be enclosed in a single IC package mounted to hybrid substrate 60. The assembly of the hybrid substrate 76 within the pulse generator case is precisely controlled to establish the orientation. The S-I, A-P, and L-M orientation markings 82, 84, and 86 may be made on the pulse generator case 78 for the convenience of the implanting physician.

The effect of 1 G of gravitational force applied directly along the sensitive axis of a stationary ADXL 50 accelerometer provides a characteristic output voltage signal level that is referenced or scaled as +1 for angular computation purposes. The effect of 1 G of gravitational force applied in precisely the opposite or negative direction to the sensitive axis provides a characteristic output voltage signal level that is referenced or scaled as –1. If the sensitive axis is oriented transversely to the direction of the gravitational force, a bias voltage level output signal should be present, and that voltage signal level is referenced or scaled as 0. The degree to which the sensitive axis is oriented away or tilted from the direction of the gravitational force can also be detected by the magnitude and polarity of the output voltage signal level deviating from the bias level scaled to 0 and below the output signal level values scaled to +1 and –1. The above-referenced publications provide instructions for scaling the voltage signal levels to the 0, +1 and –1 static level values. A microprocessor interface circuit with auto calibration of offset error and drift caused by temperature variation that may be employed in the activity circuit 62 of FIG. 1 is also described.

Other scales may be employed, depending on the signal polarities and ranges employed. The examples described below with reference to the data collected in testing and illustrated in FIGS. 7–9 employ a scale where 0 G develops a +1.000 volt DC signal, +1 G develops a +1.400 volt DC signal and –1 G develops a +0.600 volt signal.

The effect of instantaneous or AC changes due to body motion acceleration can be measured by the voltage signal output level changes per unit time. As indicated in the above-incorporated publications, the ADXL 50 can discriminate instantaneous acceleration levels up to 50 Gs, which is well in excess of the sensitivity required to detect patient footfalls regardless of the intensity level that a patient could muster. The output signal levels may be scaled to a lower range, e.g. 0 to ±2–5 G through adjustment of the internal ADXL 50 buffer amplifier or custom fabrication.

Returning to FIG. 2, the present invention may be incorporated in an IPG having a single one, two or three DC accelerometers, the selection of a single one at least including the A-P or S-I DC accelerometers 74 or 72, respectively, and preferably the A-P DC accelerometer 74. FIG. 2 thus inclusively illustrates any such combination, and the following description of the combination of all three will be understood to be inclusive of less than three for purposes of understanding the present invention. Of course, the present invention may be advantageously combined with the system for determining other body positions than stair climbing employing the output signals of the other accelerometers in combination.

When the one, two or three DC accelerometers 72, 74 or 76 of the ADXL 50 type are incorporated into a pulse generator as depicted, the sensitive axis of S-I DC accelerometer 72 is intended to be aligned, when the pulse generator 30 is implanted, as close to vertical as possible, employing the markings 82, 84, 86, for example. Thus, when standing upright and remaining still, the output signal level generated by +1 G should be realized or closely approached by the S-I DC accelerometer 72. At the same time, the output signal levels of the A-P and L-M DC accelerometers 74 and 76 should approach those representing 0 G.

When the patient lies still on his/her back or stomach, the DC signal levels of the A-P DC accelerometer 74 should approach those generated by +1 G or -1 G, respectively, (if the pulse generator case 70 is implanted with the A-P DC accelerometer positive vector pointed anteriorly) while the signal levels of the S-I and L-M DC accelerometers 72 and 76 should approach the DC signal level generated in response to 0 G. In the same fashion, the patient lying on the right and left sides will orient the sensitive axis of the L-M DC accelerometer 76 with the gravitational force to develop either the +1 G or -1 G signal level while the signal levels of the S-I and A-P DC accelerometers 72 and 74 should approach the 0 G signal level.

Deviations from the DC signal levels characteristic of +1 G, 0 G and -1 G of each DC accelerometer 72, 74 and 76 can be measured after implantation during a patient work up in these positions. The deviations may be stored in RAM 64 as adjustment values to be used by the microprocessor in weighting or otherwise processing the actual scaled output signal levels of the three DC accelerometers 72, 74 and 76 periodically supplied to the microcomputer circuit 34 through the digital controller/timer circuit 40. Moreover, the actual implantation orientations of the positive axis vectors of A-P and L-M DC accelerometers 74 and 76 can also be determined by the polarity of the signals generated. Those orientations may be stored in the microcomputer memory and employed to change the polarity of the output signal levels of the three DC accelerometers 72, 74 and 76, as necessary.

The above description provides a framework for developing a set of equations for deriving the patient's physical position while at rest and while moving in a variety of positions as described in greater detail in the above-referenced (P-3270B) application. In accordance with the present invention, less than three orthogonally disposed DC accelerometers of the type described above may be employed in stair climbing discrimination. Preferably, the output signal of the A-P DC accelerometer 74 in the range between 0 and ±1 G (depending on the orientation of gravity to the sensitive axis) and the frequency of 0–0.5 Hz is detected and employed to determine if the moving patient is leaning forward and the extent of forward lean or tilt. The A-P DC accelerometer 74 also generates recurring AC acceleration output signals in the same or higher magnitude range and a frequency of 1–10 Hz indicative of footsteps or other body motion. The combination of signals is employed in the discrimination of stair or steep incline ascending by comparison of a "Tilt Deviation" signal level to thresholds as described below. Simple bending over motion or the static forward lean of the patient in the absence of the recurring signals exceeding a threshold activity level is not determined to be stair climbing. Similarly, too great a forward lean or tilt accompanied by activity signals exceeding the threshold will not cause the stair climbing heart rate to be invoked.

Figure 6A:
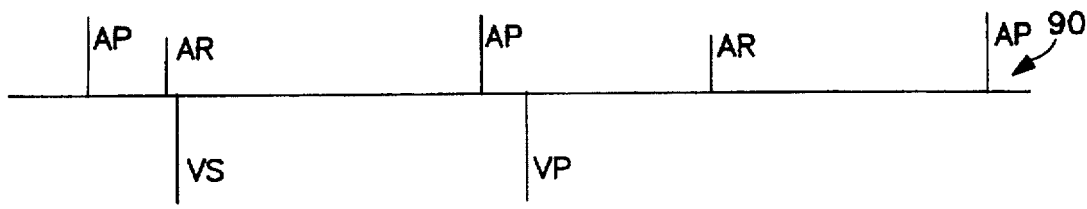
FIG. 6 is a graph illustrating the calculation of the appropriate pacing rates related to the degree of body tilt of an active patient in walking, climbing and descending a flight of stairs.
Figure 6B:
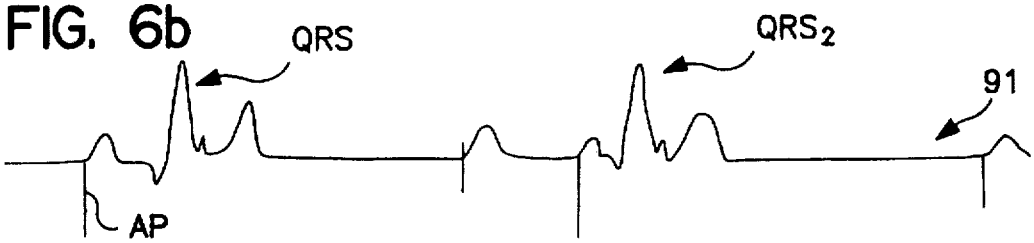
Figure 7A:
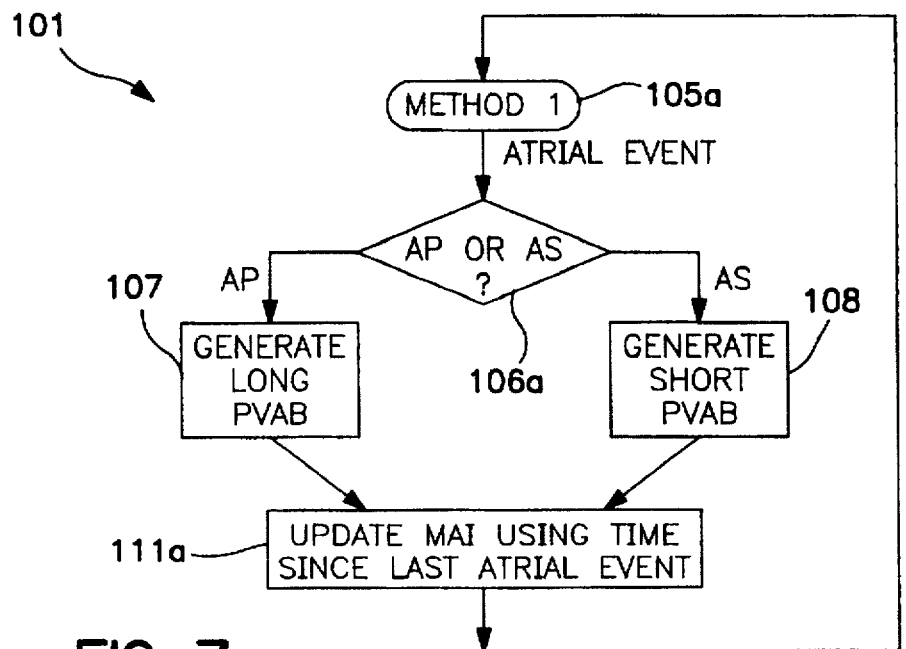
Figure 7B:
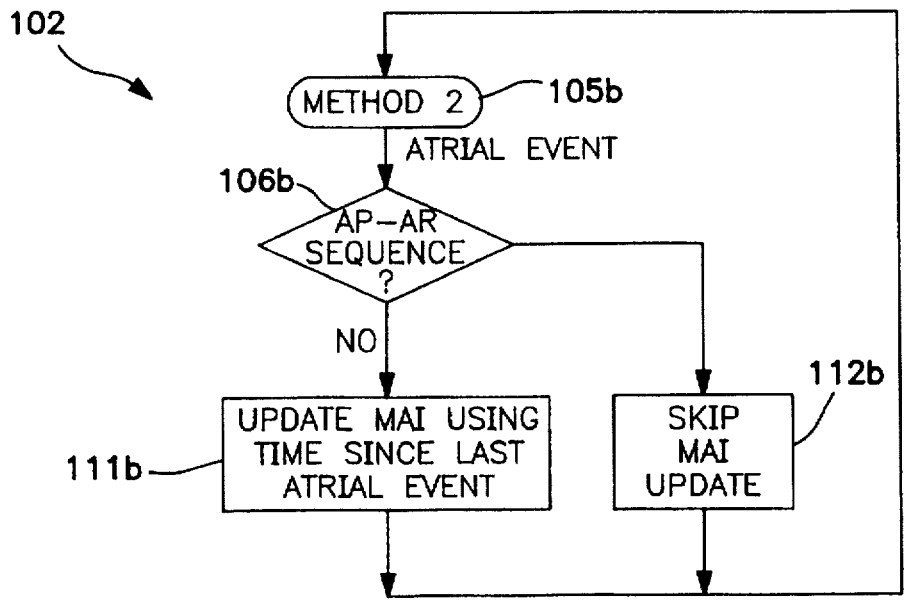
Figure 7D:
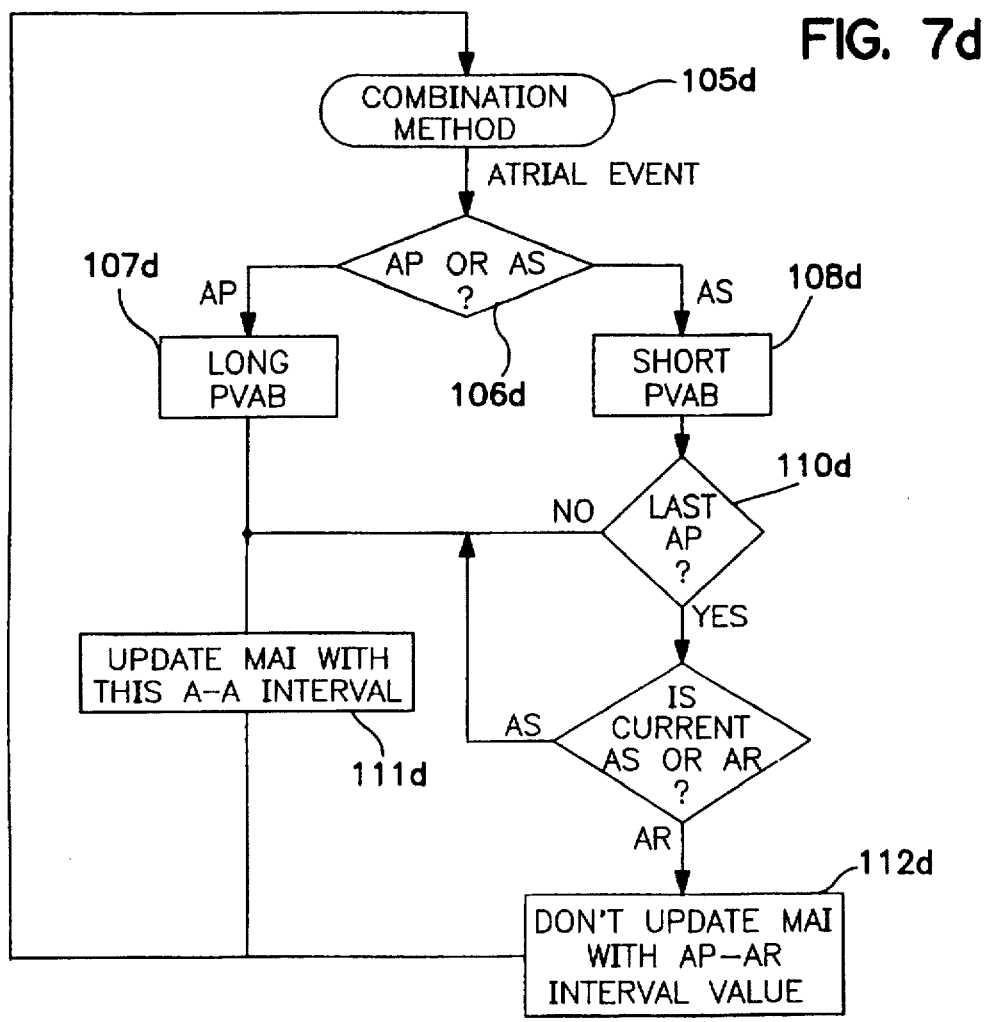

Turning to FIG. 3, it depicts a rate response overview flowchart of the algorithm incorporated into the pacemaker of FIG. 1 for deriving a physiologic "Stair Climbing" pacing rate from the output signal of the AP DC accelerometer 74. FIG. 4 is a detailed flowchart of the stair climbing discrimination step of the flowchart of FIG. 3. FIG. 5 is a detailed flowchart of the discrimination rate calculation step of the flowchart of FIG. 3. FIG. 6 illustrates the selection of the Stair Climbing Rate or an intermediate pacing rate versus a Target Rate depending on the Tilt Deviation signal level as a Pacing Rate Control signal for use in setting the pacing rate (after any rate smoothing in the flowchart of FIG. 3).

As described above, the A-P DC accelerometer 74 is oriented when the IPG case is implanted to the force of gravity so that the DC output signal level is nominally at +1.000 volts at 0 G and varies between +0.600 and +1.400 volts at -1 G and +1 G, respectively. In FIG. 3, the signal output level from the A-P DC accelerometer 74 in block 200 is sampled at a sampling frequency, e.g. 200 Hz, and applied to block 202 where the DC component "Measured Tilt" and the AC component "Activity Count" are determined over a certain sampling period, e.g. a running 2 second period. The Measured Tilt signal reflects both the DC signal level contributed by the forward lean or tilt of the patient's torso and the AC signal level that changes in magnitude as a function of the impact force from footsteps or other body motion. However, the AC signal magnitudes tend to be averaged out the sampling time period. Certain of the Measured Tilt signal levels are averaged as described below.

The current exercise activity level of the patient may be derived from a count of the activity events. An activity event is detected in step 202 when an output signal of A-P DC accelerometer 74 (or one of the other DC accelerometers 72 or 76, if present, or a combination of output signals) in the frequency range of 1–10 Hz is detected that exceeds a positive or negative scale threshold. The Activity Count is determined in a conventional process of filtering the sampled output signal in the 1–10 Hz frequency range, amplifying the filtered signal, comparing the amplified signal to a threshold level, and counting the threshold exceeding signals.

For example, the patient's footfalls cause shock waves to be transmitted through the body that drive the A-P DC accelerometer 74 to develop alternating output signals at a level exceeding the threshold level and within the specified frequency range for walking or running. Those sampled values exceeding the activity threshold level are characterized as activity events. The activity events are counted in step 202 over a running time period, e.g. 2 seconds, to derive the Activity Count. Arm and leg motion accompanying prone exercises, e.g. swimming, may also generate activity events.

In step 204, the Activity Count is employed to set the Target Rate appropriate to the estimated level of exercise. The Target Rate for pacing the patient's heart is proportional to the Activity Count and varies between the programmed pacing Lower and Upper Rates in a manner well known in the art. Target Rate is typically used to refer to a pacing rate subject to further modification as by conventional rate smoothing in physiologic pacemakers.

Since the Activity Count for stair ascending may be equal to or less than that for flat surface walking or stair descending, the Target Rate may be insufficient for stair ascending which requires greater cardiac output. Therefore, it is appropriate to employ a substitute Stair Climbing Rate (again subject to modification before being used as the actual pacing rate). Since certain other activities may also generate an Activity Count mimicking walking or running, the determination of the posture of the patient with the same or a set of the DC accelerometers is important to a determination that the Target Rate or the Stair Climbing Rate (and intermediate rates therebetween) is appropriate.

In accordance with the preferred embodiment, it is contemplated that a fixed Stair Climbing Rate may be programmed in for the individual patient. The Stair Climbing Rate is invoked if stair climbing is detected and if the patient's activity level itself does not dictate a higher Target Rate. For example, the activity level due to the AC acceleration component contribution may signify light to heavy exercise levels dictating moderate to high Target Rate of pacing. If the patient is moving rapidly, it may be immaterial that the patient is also climbing stairs or a steep grade, since the Target Rate may exceed the preprogrammed Stair Climbing rate in that instance. In a further variation where the Stair Climbing Rate does exceed the Target Rate, the actual intermediate pacing rate may be selected to fall between the programmed Stair Climbing Rate and the calculated Target Rate.

The stair climbing discrimination step 206 (shown in the flowchart of FIG. 4) employs the Measured Tilt signal to make a determination that the patient is or is not climbing stairs or an incline sufficiently steep and/or long to cause the patient to lean forward. The selection of the Stair Climbing Rate, the Target Rate or an intermediate rate for pacing the patient is determined in step 208 (shown in the flowchart of FIG. 5). Then, in step 210 of FIG. 3, the pacing rate is modified to provide rate smoothing in accelerating from the lower Target Rate and the greater Stair Climbing or intermediate rate at the onset of stair climbing and decelerating back to the Target Rate on completion of stair climbing, employing well known rate smoothing techniques.

Turning to FIG. 4, the stair climbing discrimination steps included in step 208 commence with the determination of whether the patient is active in decision step 300 from the presence of an Activity Count. If no Activity Count is present, then the "not stair climbing" determination is made or stated in step 302. No change in the Target Rate (in this case, the programmed Lower Rate) is made, after the steps of the flowchart of FIG. 5 are completed.

If the patient is active, then a Tilt Average is calculated in block 304 from the sum of the amplitudes of the Measured Tilt signals occurring while the Activity Count is satisfied (and as long as the Tilt Deviation does not exceed an OTW Upper value as described below) divided by the number of samples. For example, a number of samples, e.g. 300 samples, may be obtained on a running basis and accumulated on a FIFO basis and the Tilt Average calculated therefrom. Typically, the Tilt Average will be derived when a patient is walking on a flat surface before climbing stairs and will reflect a DC signal level contribution only to the extent that the IPG is tilted from the A-P axis direction 84 at the implantation site or the patient walks with a forward stoop. As mentioned above, any deviation due to inclination of the sensitive axis of the A-P DC accelerometer at the implant site may be determined during patient work up while the patient is standing still and upright. In the example described above, the observed deviation from +1.000 volts may employed as a weighting factor to adjust the Tilt Average DC signal level component back to near the =1.000 volt level. However, in any given case, it may not be necessary to do the patient work up and make the adjustment.

After a Tilt Average is calculated, a "Tilt Deviation" signal is then calculated in block 306 by subtracting the Measured Tilt signal from the Tilt Average. If there is no significant difference, then the patient is continuing to walk or run without forward lean characteristic of stair or steep incline ascending and the Tilt Average continues to be accumulated. In this way, the onset of a DC component increase in the Measured Tilt signal attributable to patient forward lean can be detected by comparison to the Measured Tilt to the Average Tilt accumulated while the patient remains active.

In step 308, the Tilt Deviation signal level is compared to an Outer Tilt Window (OTW) previously derived from the output signal of the A-P DC accelerometer 74 during the previous patient work up. The OTW is an outer range of Tilt Deviations signal values between an OTW Upper and OTW Lower value derived from the Tilt Deviation signals generated in the work up as the patient ascends a set of steps or a stair step exercise machine for an average flight of stairs and is stored in the memory 68 of the microcomputer circuit 34. An inner Tilt Window (ITW) representing a narrower range of the Tilt Deviation signal values between an ITW Lower and an ITW Upper value may also be stored in memory 68. These ranges of values may alternatively be derived based on population studies and programmed by the physician. The relation of the OTW and ITW in the selection of the pacing rate is explained further below in reference to FIGS. 5 and 6.

If the Tilt Deviation signal is not within the OTW, then it is determined in step 310 that the patient is not stair climbing, and the tilt deviation is checked against the OTW Upper value in decision step 312. When OTW Upper value is exceeded, the patient is likely prone and exercising, e.g. by swimming. In such a case, the Target Rate is employed in step 210 of FIG. 3 as described below. Moreover, the Tilt Average is not updated in step 312.

Returning to step 308, if the Tilt Deviation is within the OTW, then the patient is determined to be stair climbing in step 314. The Tilt Average signal derived in step 202 is then updated in memory in step 316 by the current Measured Tilt.

Turning to FIG. 5, the discrimination rate calculation step 208 commences with the stair climbing decision step 314. If stair climbing was determined in step 310, then the Stair Climbing Rate is compared to the Target Rate in decision step 316. If either "not stair climbing" is determined in step 318 or if the Target Rate exceeds the Stair Climbing Rate in step 320, then the instruction "do not change target rate" is generated in step 322, and the Target Rate is employed in step 210. This is also the path that would be followed from step 302 or step 312 if the Tilt Deviation exceeds the OTW Upper value.

In step 320, if the Stair Climbing Rate exceeds the Target Rate, then the Tilt Deviation is compared to the ITW in step 324. If the Tilt Deviation is within the ITW, then the pacing rate is changed to the Stair Climbing Rate in step 326. If the Tilt Deviation is outside the ITW, then the pacing rate is changed to an interpolation of the two rates in step 328 through the use of a look up table of interpolation values stored in the memory 68 or a calculation.

Turning to FIG. 6, it depicts one example of the OTW and ITW signal ranges that can be employed to determine a Pacing Rate control signal selected from the Target Rate a higher (in this example) Stair Climbing Rate, and intermediate rates in between these two flat rates. The Tilt Window Deviations in mV vary from the nominal "0" value or 1.000 volts as described above. The Target Rate applies outside the OTW Lower and OTW Upper range values of the Tilt Deviation. A higher Stair Climbing Rate applies within the ITW Upper and ITW Lower range values of the Tilt Deviation. The interpolated intermediate rates prevail in the range of Tilt Deviation values between the ITW Lower and OTW Lower values as well as the ITW Upper and ITW Upper values.

In FIG. 6, the Stair Climbing Rate of 120 bpm exceeds the Target Rate of 90 bpm, and therefore controls, if the Tilt Deviation is within the ITW. Tilt Deviations of 20 mV and 110 mV, for example, fall outside both the Lower and Upper limits of the OTW and ITW, and the pacing rate is therefore controlled by the Target Rate of 90 bpm. A Tilt Deviation of 120 mV falls within the ITW, and the pacing rate is controlled by the Stair Climbing Rate (SCR) of 120 bpm. Within the lower portion of the OTW, between 30–60 mV, the intermediate pacing rate control signal falls between 90–120 bpm. A formula for determining the intermediate pacing rate (IPR) control signal in this range is:

$$IPR = \frac{(SCR - TR)(\text{Tilt Deviation} - OTWL)}{(ITWL - OTWL)} + TR$$

Similarly, between 80–100 mV, the pacing rate control signal falls between 120–90 bpm. A formula for determining the intermediate pacing rate (IPR) control signal in this range is:

$$IPR = \frac{(SCR - TR)(OTWU - \text{Tilt Deviation})}{(OTWU - ITWU)} + TR$$

From the above description, it may be seen that the discrimination between stair climbing and stair descending or walking on a flat surface is sufficient without making a positive determination that the patient is descending steps or a steep incline. The Target Rate suffices as a stair or incline descending pacing rate. If the Target Rate reflects rapid movement, then it will suffice for any of the three activities.

Referring back to FIG. 1, the Target Rate, Stair Climbing Rate or the intermediate pacing rate derived in this fashion provide pacing rate control signals derived from the determination of the patient body posture and the patient activity level correlated to the physiologic demand on the patient's heart from which physiologic escape intervals establishing the physiologic pacing rate are developed by the digital controller/timer circuit 40 and the microcomputer circuit 34 operating as described above. The pacing pulses are generated by the output amplifier circuit 36 at the physiologic pacing rate, and are applied to the patient's heart 10 through the leads 12 and 14.

Figure 8:
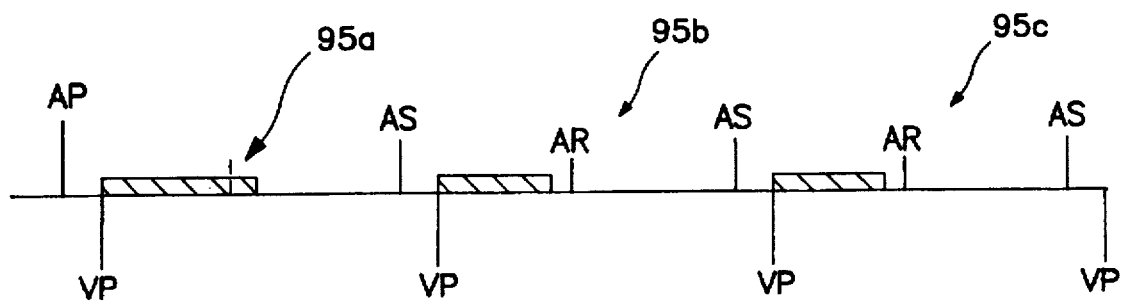
Figure 9:
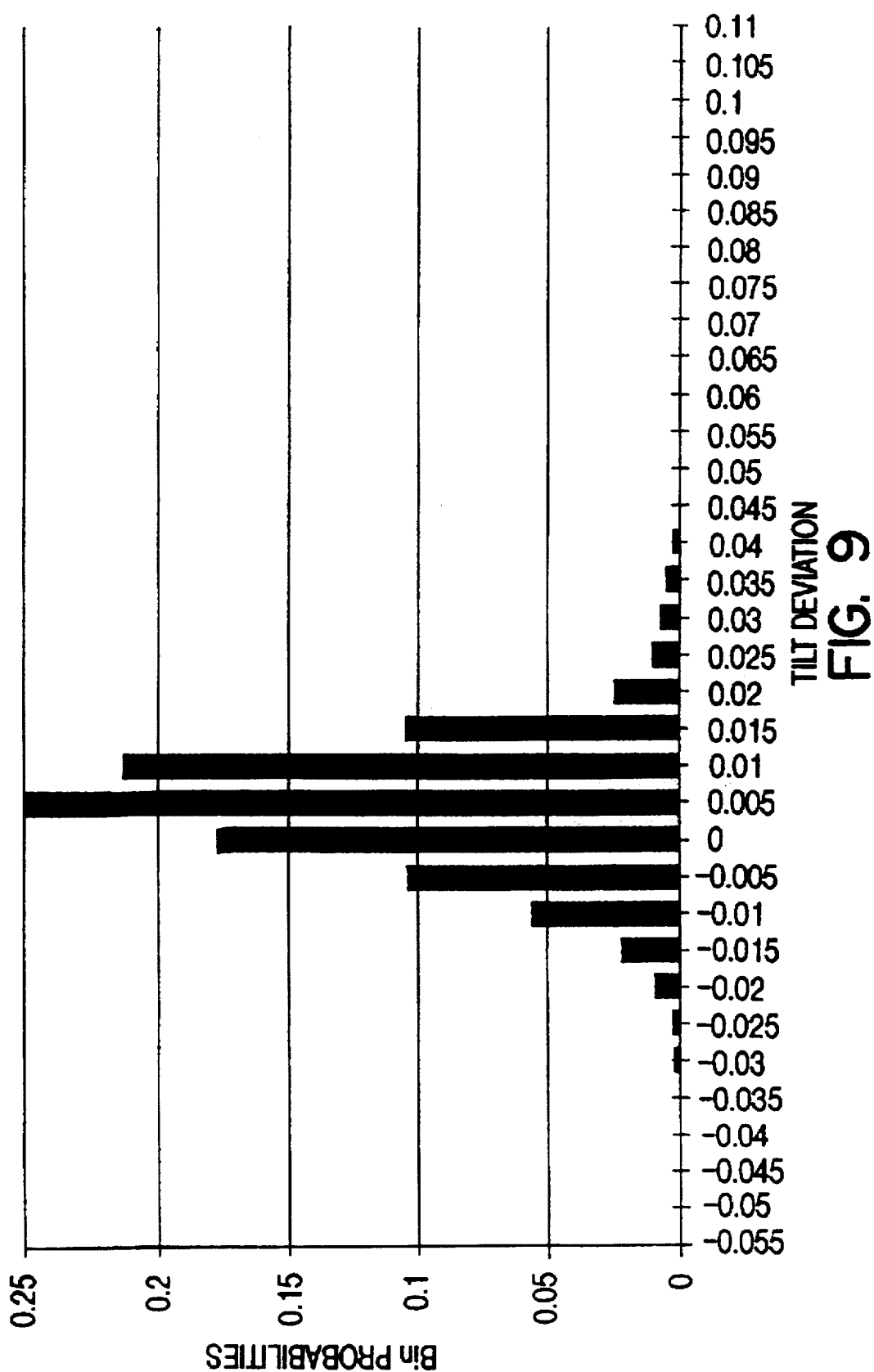

Turning now to FIGS. 7–9, they depict, in graphical form, the Tilt Deviation distributions achieved in 19 strap-on tests of test subjects derived using the above process during stair climbing, stair descending and normal walking. The three distributions demonstrate the sensitivity of the discrimination that can be achieved from the DC component of the output signal of the DC accelerometer.

Figure 10:
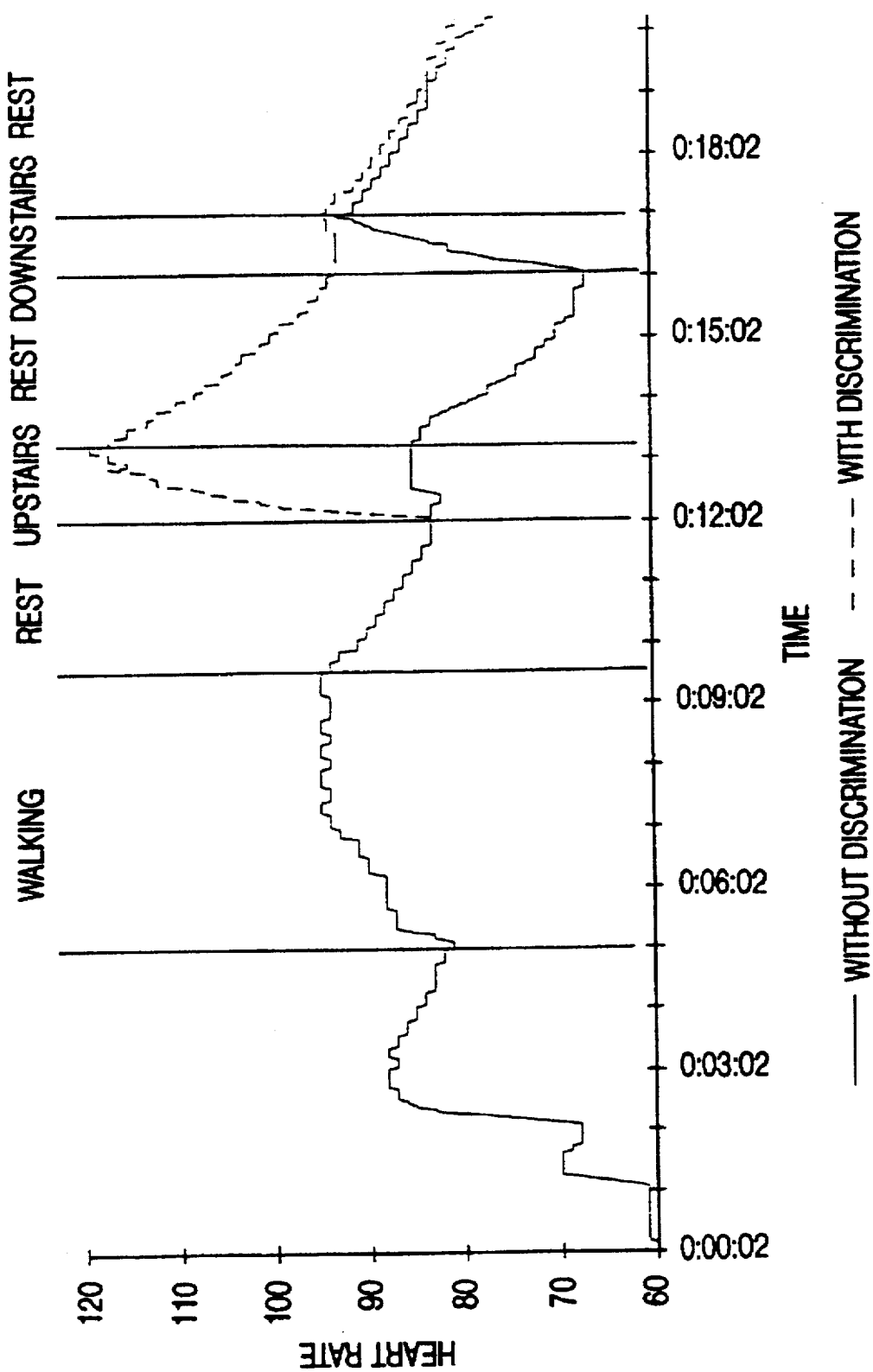
FIG. 10 is a graph illustrating the delivery of the appropriate pacing rates related to the degree of body tilt of an active patient in walking, climbing and descending a flight of stairs.

The data derived from a strap-on test of a volunteer subject engaged in walking, resting, climbing upstairs, resting, descending stairs and again resting over time is also depicted in FIG. 10. The target pacing rate (without discrimination) and the stair climbing rate (with discrimination) generated following the above algorithm from the output signals of the A-P DC accelerometer 74 are depicted. As can be seen, the stair climbing rate increase is appropriately effected without inappropriately increasing the stair descending pacing rate.

It should be noted that the stair climbing detection may also trigger storage of episodic data in microcomputer circuit memory for later telemetry out and analysis by the physician. The appropriateness of the Stair Climbing Rate and the ITW and OTW windows can be analyzed for the particular patient. The stair climbing discrimination of the present invention may be programmed off in the event that the patient does not benefit from it.

Other adjustments could be made to pacemaker programming based on a determination of patient tilt. While this application specifically highlights the advantage of having this information from an accelerometer sensor to distinguish stair climbing from other activities, it can also find value in providing redundant or confirmatory information regarding the onset of vasovagal syncope, orthostatic hypotension and for distinguishing between sitting up and standing.

For example, the amount of rapid rate drop required to trigger a vasovagal syncope response from an implanted pacemaker could be decreased if the tilt sensor indicates that a patient has been sitting down or lying down for a given period of time and is now moving to a standing position. The possibility of a VVS (vasovagal syncope) episode is greater during standing, therefore, the rapid rate drop sensitivity and specificity could be improved by decreasing the amount of rapid rate drop required for indicating a VVS condition if there is a static indication of standing for a given (preferably physician recommended) period of time. Also increasing the amount of rapid rate drop required to determine the existence of a VVS condition is preferred if the sensor indicates static posture of lying (again for a preferably physician recommended period of time). By including such an indicator, the VVS detector circuit (which could be one as is described in Markowitz, U.S. Pat. No. 5,501,701 or Sutton U.S. Pat. No. 5,284,491) can be made responsive enough to trigger a pacemaker response before the patient faints.

Orthostatic hypotensive patients suffer from a sudden drop of venous return and arterial pressure during orthostatic stress. The tilt sensor could be used to measure the degree of orthostatic stress based on the patient tilt and increase the pacing rate as the apparent orthostatic stress increases. The increased pacing rate would augment the venous return and alleviate orthostatic symptoms.

Figure 11:
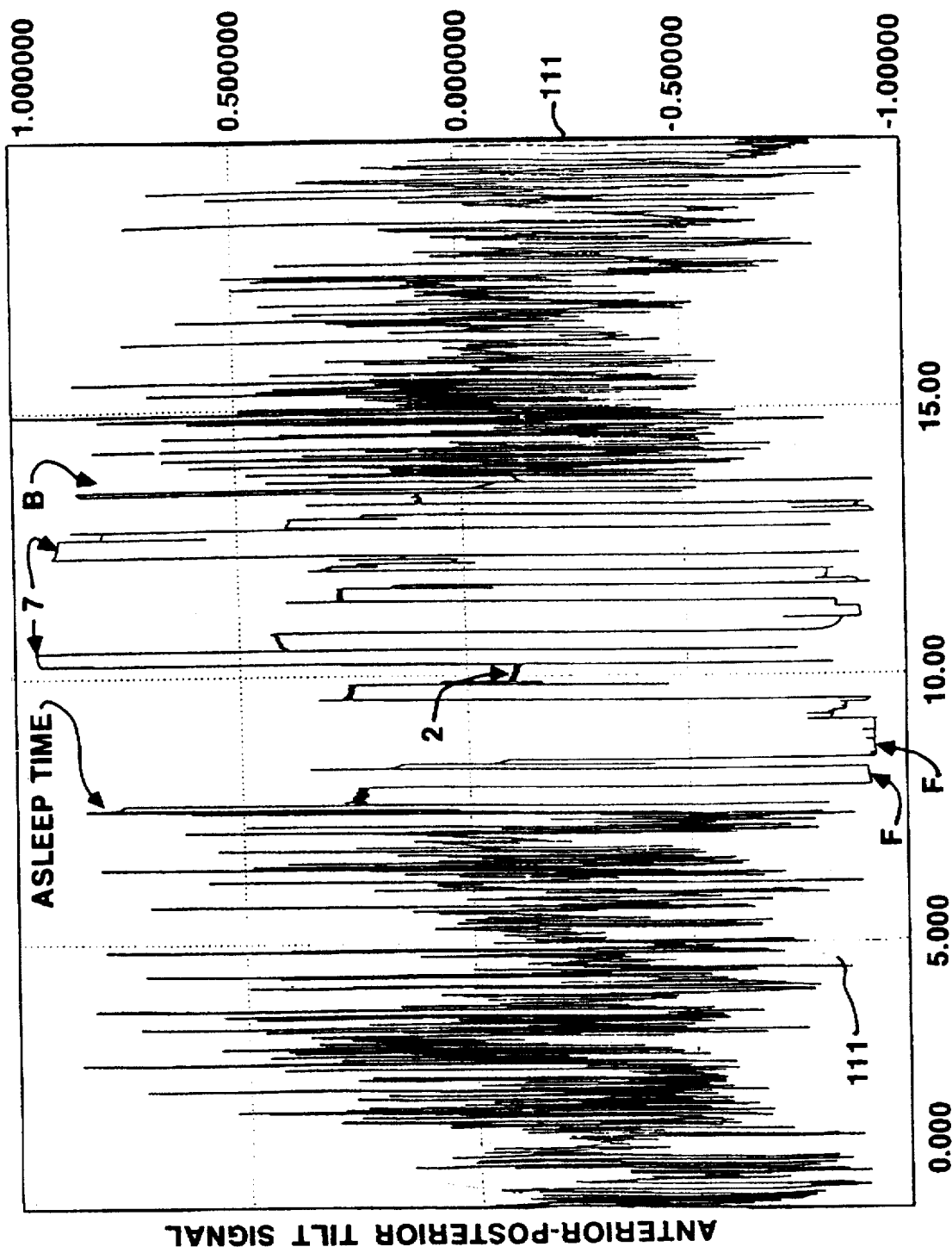
FIG. 11 is a graph of time versus signal level for the anterior-posterior tilt signal for one patient.

The variation in the tilt signal can be used as a circadian rhythm detector. The variation in the tilt signal is much greater during awake periods when the subject is bending over, sitting, standing, etc. than when the subject is resting or sleeping. See FIG. 11 which shows that the size and frequency of the offset found in the DC signal is much greater during awake time for patients. In FIG. 11, the time the patient is asleep 110 shows little variance in the anterior-posterior (AP) signal 111. In fact it appears to rest at one pole when the patient lies on his Face (or prone) or Back (or supine). Further, in a side oriented quiescent state (S) the A-P signal is about zero.

Accordingly, a flag could be set in the pacemaker or other implantable device memory that indicates whether the patient is awake or asleep so that therapy and diagnostics can be adjusted or mated to accommodate this change in patient diurnal cycle time. Quiet time periods are good for testing threshold levels of pulse width and amplitude and may also be used to turn off rate response or other functions to save battery power during sleep. If used in an implanted drug pump, evening or sleep level dosages may be varied from daytime or active cycle doses, thus accommodating patient needs.

Also, during times of activity, different base rates can be selected such that the patient maintains a higher minimum base rate when in a sitting position than in a lying position and, experiences an even higher base or minimum rate for a standing posture. This minimum pacing rate should be overridden by an activity sensor showing that the patient activity level (movement over time as determined by the AC or short term component of the A-P accelerometer or through some other physiologic activity measurement) calls for greater cardiac output than the base rate in the particular position provides.

Generally then, it is clear that employing a signal that indicates a degree of tilt can be accomplished in many ways to alter the pacing strategy delivered to the patient.

The general possibility has been discussed in a PACE Magazine article (Nov. 1994, pp. 1933–1938) detailing Pacesetter's use of activity variance during sleep. However, its use in conjunction with the improved reliability of tilt monitoring is not seen anywhere.

Variations and modifications to the present invention may be possible given the above disclosure. For example, the present invention is not limited to any particular pacing mode, and can function with prior art modes such as DDDR, AAIR, VVR and DDIR. It will also be understood that the present invention may be implemented in dual-chamber pacemakers, cardioverters, defibrillators and the like. However, all such variations and modifications are intended to be within the scope of the invention claimed by this letters patent.

What is claimed is:

1. A method of pacing a patient's heart at a pacing rate dependent on patient activity and posture particularly during stair climbing comprising the steps of:

deriving a body posture tilt signal having a characteristic varying with the degree to which the patient posture is in an upright stance or leaning forward;

detecting patient footsteps;

deriving a patient activity signal having a signal level dependent on the frequency of patient footsteps recurring over a time unit;

deriving a rate control signal from the body posture tilt signal and the patient activity signal correlated to the physiologic demand on the patient's heart;

defining physiologic escape intervals as a function of the rate control signal to establish a physiologic pacing rate;

generating pacing pulses at the physiologic pacing rate; and applying the pacing pulses to the patient's heart.

2. The method of claim 1 wherein the step of deriving a body posture tilt signal further comprises measuring the forces of acceleration in the anterior-posterior axis of the patient's body recurring in a first predetermined low frequency range and deriving a measured tilt signal therefrom.

3. The method of claim 2 wherein the step of detecting patient footsteps further comprises measuring the forces of acceleration in the anterior-posterior axis of the patient's body recurring in a second predetermined frequency, range higher in frequency than said first predetermined low frequency range and deriving the patient activity signal therefrom.

4. The method of claim 3 wherein the steps of deriving a body posture tilt signal and detecting patient footsteps further comprise the steps of:

mounting a solid state DC accelerometer having a sensitive axis of deflection and providing an output signal varying in magnitude in response to the DC force of gravity and AC forces of acceleration applied along the sensitive axis in a pacemaker pulse generator;

implanting the pulse generator in the patient with the second sensitive axis generally aligned with the patient's anterior-posterior body direction while the patient is in the upright stance;

deriving a forward tilt signal from the output signal of a polarity and magnitude varying in response to the DC force of gravity and representative of the degree to which the patient is leaning forward from an upright stance; and detecting the patient footsteps from the output signal varying in magnitude in response to the AC forces of acceleration applied along the sensitive axis.

5. The method of claim 4 wherein the step of deriving a pacing rate control signal from the body posture tilt signal and the patient activity signal correlated to the physiologic demand on the patient's heart further comprises:

providing a target rate control signal for pacing the patient's heart as a function of the patient activity signal;

providing a stair climbing rate control signal;

comparing the body posture tilt signal to a tilt window;

when the body posture tilt signal is within the tilt window, employing the stair climbing rate control signal as the pacing rate control signal; and when the body posture tilt signal is outside the tilt window, employing the target rate control signal as the pacing rate control signal.

6. The method of claim 5 further comprising the step of comparing the target rate control signal with the stair climbing rate control signal and employing the greater as the pacing rate control signal.

7. The method of claim 1 wherein the step of deriving a pacing rate control signal from the body posture tilt signal and the patient activity signal correlated to the physiologic demand on the patient's heart further comprises:

providing a target rate control signal for pacing the patient's heart as a function of the patient activity signal;

providing a stair climbing rate control signal;

comparing the body posture tilt signal to a tilt window;

when the body posture tilt signal is within the tilt window, employing the stair climbing rate control signal as the pacing rate control signal; and when the body posture tilt signal is outside the tilt window, employing the target rate control signal as the pacing rate control signal.

8. The method of claim 7 further comprising the step of comparing the target rate control signal with the stair climbing rate control signal and employing the greater as the pacing rate control signal.

9. The method of claim 1 wherein the step of deriving a pacing rate control signal from the body posture tilt signal and the patient activity signal correlated to the physiologic demand on the patient's heart further comprises:

providing a target rate control signal for pacing the patient's heart as a function of the patient activity signal;

providing a stair climbing rate control signal;

comparing the body posture tilt signal to an inner and an outer tilt window;

when the body posture tilt signal is within the inner and the outer tilt windows, employing the stair climbing rate control signal as the pacing rate control signal;

when the body posture tilt signal is outside the outer tilt window, employing the target rate control signal as the pacing rate control signal; and when the body posture tilt signal is within the outer tilt window and outside the inner tilt window, deriving an intermediate rate control signal and employing the intermediate rate control signal as the pacing rate control signal.

10. The method of claim 9 further comprising the step of comparing the target rate control signal with the stair climbing rate control signal and employing the greater as the pacing rate control signal whether or not the body posture tilt signal is within the inner or outer tilt windows.

11. The method of claim 1 wherein the steps of deriving a body posture tilt signal and detecting patient footsteps further comprise the steps of:

mounting a solid state DC accelerometer having a sensitive axis of deflection and providing an output signal varying in magnitude in response to the DC force of gravity and AC forces of acceleration applied along the sensitive axis in a pacemaker pulse generator;

implanting the pulse generator in the patient with the second sensitive axis generally aligned with the patient's anterior-posterior body direction while the patient is in the upright stance;

deriving a forward tilt signal from the output signal of a polarity and magnitude varying in response to the DC force of gravity and representative of the degree to which the patient is leaning forward from an upright stance; and detecting the patient footsteps from the output signal varying in magnitude in response to the AC forces of acceleration applied along the sensitive axis.

12. The apparatus of claim 1 wherein the means for deriving a body posture tilt signal further comprises means for measuring the forces of acceleration in the anterior-posterior axis of the patient's body recurring in a first predetermined low frequency range and deriving a measured tilt signal therefrom.

13. The apparatus of claim 12 wherein the means for detecting patient activity further comprises means for measuring the forces of acceleration in the anterior-posterior axis of the patient's body recurring in a second predetermined frequency range higher in frequency than said first predetermined low frequency range and deriving the patient activity signal therefrom.

14. The apparatus of claim 13 wherein the means for deriving a body posture tilt signal and the means for detecting patient activity further comprise:

means for responding to the force of gravity on the patient's body along a generally anterior-posterior axis of the patient's body and deriving a forward tilt signal therefrom of a polarity and magnitude representative of the degree to which the patient is leaning forward from an upright stance; and means for measuring forces of acceleration in the patient's body due to patient footsteps and deriving a patient activity signal therefrom representative of patient footsteps.

15. The apparatus of claim 14 wherein the means for deriving a pacing rate control signal from the body posture tilt signal and the patient activity signal correlated to the physiologic demand on the patient's heart further comprises:

means for providing a target rate control signal for pacing the patient's heart as a function of the patient activity signal;

means for providing a stair climbing rate control signal;

means for comparing the body posture tilt signal to a tilt window;

means for employing the stair climbing rate control signal as the pacing rate control signal when the body posture tilt signal is within the tilt window; and means for employing the target rate control signal as the pacing rate control signal when the body posture tilt signal is outside the tilt window.

16. The apparatus of claim 15 further comprising means for comparing the target rate control signal with the stair climbing rate control signal and employing the greater as the pacing rate control signal.

17. Apparatus for pacing a patient's heart at a pacing rate dependent on patient activity and posture particularly during stair climbing comprising:

means for deriving a body posture tilt signal having a characteristic varying with the degree to which the patient posture is in an upright stance or leaning forward;

means for detecting patient activity and for deriving a patient activity signal having a signal level dependent on the frequency and magnitude of patient activity;

means for deriving a rate control signal from the body posture tilt signal and the patient activity signal correlated to the physiologic demand on the patient's heart;

means for defining physiologic escape intervals as a function of the rate control signal to establish a physiologic pacing rate;

means for generating pacing pulses at the physiologic pacing rate; and means for applying the pacing pulses to the patient's heart.

18. The apparatus of claim 17 wherein the means for deriving a pacing rate control signal from the body posture tilt signal and the patient activity signal correlated to the physiologic demand on the patient's heart further comprises:

means for providing a target rate control signal for pacing the patient's heart as a function of the patient activity signal;

means for providing a stair climbing rate control signal;

means for comparing the body posture tilt signal to a tilt window;

means for employing the stair climbing rate control signal as the pacing rate control signal when the body posture tilt signal is within the tilt window; and means for employing the target rate control signal as the pacing rate control signal when the body posture tilt signal is outside the tilt window.

19. The apparatus of claim 18 further comprising the means for comparing the target rate control signal with the stair climbing rate control signal and employing the greater as the pacing rate control signal.

20. The apparatus of claim 17 wherein the means for deriving a pacing rate control signal from the body posture tilt signal and the patient activity signal correlated to the physiologic demand on the patient's heart further comprises:

means for providing a target rate control signal for pacing the patient's heart as a function of the patient activity signal;

means for providing a stair climbing rate control signal;

means for comparing the body posture tilt signal to a tilt window;

means for employing the stair climbing rate control signal as the pacing rate control signal when the body posture tilt signal is within the tilt window;

means for employing the target rate control signal as the pacing rate control signal when the body posture tilt signal is outside the tilt window; and means for deriving an intermediate rate control signal and employing the intermediate rate control signal as the pacing rate control signal when the body posture tilt signal is within the outer tilt window and outside the inner tilt window.

21. The apparatus of claim 20 further comprising means for comparing the target rate control signal with the stair climbing rate control signal and employing the greater as the pacing rate control signal whether or not the body posture tilt signal is within the inner or outer tilt windows.

22. The apparatus of claim 12 wherein the means for deriving a body posture tilt signal and the means for detecting patient activity further comprise:

means for responding to the force of gravity on the patient's body along a generally anterior-posterior axis of the patient's body and deriving a forward tilt signal therefrom of a polarity and magnitude representative of the degree to which the patient is leaning forward from an upright stance; and means for measuring forces of acceleration in the patient's body due to patient footsteps and deriving a patient activity signal therefrom representative of patient footsteps.

23. In a pacemaker pulse generator adapted to be implanted in a patient's body, apparatus for pacing a patient's heart at a pacing rate dependent on patient activity and body posture particularly to provide adequate cardiac output during stair climbing comprising:

means for responding to the force of gravity on the patient's body and deriving a tilt signal therefrom of a polarity and magnitude representative of the degree to which the patient is leaning forward from an upright stance;

means for measuring forces of acceleration in the patient's body due to patient footsteps and deriving a patient activity signal therefrom representative of patient footsteps;

means operable in the presence of the tilt signal and the activity signal for providing a stair climbing rate control signal correlated to the physiologic demand on the patient's heart appropriate for patient stair ascending;

means for defining physiologic escape intervals as a function of the stair climbing rate control signals to establish a physiologic pacing rate;

means for generating pacing pulses at the physiologic pacing rate; and means for applying the pacing pulses to a chamber of a patient's heart.

24. The pulse generator of claim 23 wherein said measuring means further comprises:

a DC accelerometer mounted in said pulse generator and having an anterior-posterior sensitive axis of deflection, whereby said pulse generator may be implanted with the anterior-posterior sensitive axis generally aligned to a patient's anterior-posterior body direction while in a standing upright posture, said DC accelerometer providing the tilt signal varying in magnitude in response to the DC force of gravity and polarity in response to the tilt of the sensitive axis with respect to the direction of the force of gravity.

25. The pulse generator of claim 24 wherein said rate control signal providing means further comprises:

means for defining a tilt window of a range of tilt signal values; and means operable in the presence of an activity signal for comparing the magnitude of the tilt signal to said tilt signal window and for determining that the patient is climbing stairs when the tilt signal value falls within the tilt window range.

26. The pulse generator of claim 25 wherein the means for providing a stair climbing rate control signal further comprises:

means for providing a target rate control signal for pacing the patient's heart as a function of the patient activity signal;

means for providing a stair climbing rate control signal;

means for comparing the tilt signal to a tilt window;

means for employing the stair climbing rate control signal as the pacing rate control signal when the tilt signal is within the tilt window; and means for employing the target rate control signal as the pacing rate control signal when the tilt signal is outside the tilt window.

27. The apparatus of claim 26 further comprising the means for comparing the target rate control signal with the stair climbing rate control signal and employing the greater as the pacing rate control signal.

* * * * *

UNITED STATES PATENT AND TRADEMARK OFFICE
CERTIFICATE OF CORRECTION

PATENT NO. : 5,725,562
DATED : March 10, 1998
INVENTOR(S) : Todd J. Sheldon

It is certified that error appears in the above-identified patent and that said Letters Patent is hereby corrected as shown below:

Title page, item [73] Assignee: should be inserted to read:
Medtronic, Inc. Minneapolis, Minn.--

Signed and Sealed this

Ninth Day of March, 1999

Attest:

Attesting Officer

Q. TODD DICKINSON

Acting Commissioner of Patents and Trademarks